(12) United States Patent
Hon

(10) Patent No.: US 12,274,301 B2
(45) Date of Patent: *Apr. 15, 2025

(54) ELECTRONIC CIGARETTE

(71) Applicant: FONTEM VENTURES B.V., Amsterdam (NL)

(72) Inventor: Lik Hon, Beijing (CN)

(73) Assignee: FONTEM VENTURES B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/486,966

(22) Filed: Oct. 13, 2023

(65) Prior Publication Data

US 2024/0108068 A1    Apr. 4, 2024

Related U.S. Application Data

(63) Continuation of application No. 17/136,611, filed on Dec. 29, 2020, now Pat. No. 11,805,816, which is a continuation of application No. 16/745,249, filed on Jan. 16, 2020, now Pat. No. 11,044,944, which is a continuation of application No. 15/902,712, filed on Feb. 22, 2018, now Pat. No. 10,588,353, which is a continuation of application No. 15/091,017, filed on
(Continued)

(30) Foreign Application Priority Data

Feb. 11, 2009    (CN) .......................... 200920001296.3

(51) Int. Cl.
| | | |
|---|---|---|
| A24F 40/46 | (2020.01) | |
| A24F 40/10 | (2020.01) | |
| A24F 40/40 | (2020.01) | |
| A24F 40/42 | (2020.01) | |
| A24F 40/44 | (2020.01) | |
| A61M 11/04 | (2006.01) | |
| A61M 15/06 | (2006.01) | |
| A61M 16/00 | (2006.01) | |
| H05B 3/00 | (2006.01) | |
| H05B 3/06 | (2006.01) | |

(52) U.S. Cl.
CPC .............. *A24F 40/46* (2020.01); *A24F 40/40* (2020.01); *A24F 40/42* (2020.01); *A24F 40/44* (2020.01); *A61M 11/041* (2013.01); *A61M 11/042* (2014.02); *A61M 15/06* (2013.01); *H05B 3/0014* (2013.01); *H05B 3/06* (2013.01); *A24F 40/10* (2020.01); *A61M 2016/0024* (2013.01); *A61M 2205/8206* (2013.01)

(58) Field of Classification Search
None
See application file for complete search history.

(56) References Cited

PUBLICATIONS

IP Office Japan, Application No. 20230148861, Notice of Rejection Grounds, Nov. 5, 2024.
(Continued)

*Primary Examiner* — Phu H Nguyen
(74) *Attorney, Agent, or Firm* — Perkins Cole LLP; Kenneth H. Ohriner

(57) ABSTRACT

An atomizing electronic cigarette has an atomizing core component and a liquid storage component. including an electric heater. The electric heater may have a through hole aligned with a channel passing through the liquid storage component. The cigarette can heat and uniformly vaporize liquid from the liquid storage component, with the user inhaling the vaporized liquid. The vapor generated by the atomizing process may be cooled as it flows through the channel.

12 Claims, 2 Drawing Sheets

Related U.S. Application Data

Apr. 5, 2016, now Pat. No. 10,383,366, which is a continuation of application No. 14/307,663, filed on Jun. 18, 2014, now Pat. No. 9,320,300, which is a continuation of application No. 13/208,257, filed on Aug. 11, 2011, now abandoned, which is a continuation of application No. PCT/CN2010/000125, filed on Jan. 28, 2010.

(56) References Cited

PUBLICATIONS

IP Office Korea, Application No. 10-2023-7013295, Notice of Preliminary Rejection, Jan. 16, 2024.
IP Office Korea, Application No. 10-2021-7018393, Appeal Decision, Mar. 21, 2024.

ELECTRONIC CIGARETTE

CROSS-REFERENCE TO RELATED APPLICATIONS

This application is a continuation of U.S. application Ser. No. 17/136,611, filed Dec. 29, 2020, which is a continuation of U.S. application Ser. No. 16/745,249, filed Jan. 16, 2020, now U.S. Pat. No. 11,044,944, which is a continuation of U.S. application Ser. No. 15/902,712, filed Feb. 22, 2018, now U.S. Pat. No. 10,588,353, which is a continuation of U.S. application Ser. No. 15/091,017, filed Apr. 5, 2016, now U.S. Pat. No. 10,383,366, which is a continuation of U.S. application Ser. No. 14/307,663, filed Jun. 18, 2014, now U.S. Pat. No. 9,320,300, which is a continuation of U.S. application Ser. No. 13/208,257 filed Aug. 11, 2011 and now abandoned, which is a continuation of International Application No. PCT/CN2010/000125, filed Jan. 28, 2010, which claims priority to Chinese Patent Application No. 200920001296.3, filed Feb. 11, 2009. Each of these applications is incorporated herein by reference.

BACKGROUND OF THE INVENTION

As a cigarette substitute, atomizing electronic cigarettes have occupied a large percentage of the market for smoking substitute products. The improvement of atomizing electronic cigarette technology is a prerequisite for widespread application and acceptance of electronic cigarettes.

At present, the existing atomizing electronic cigarettes still have many problems and shortcomings, for example, poor atomization, large liquid drops in the final atomized smoke, nonuniform smoke caused by different sizes of liquid drops, too much moisture in the smoke, poor mouthfeel, etc. In some conditions, the smoke is at a high temperature because of insufficient cool-down and will cause discomfort.

The above problems cause significant differences between real cigarettes and electronic cigarettes for smokers, which is not conducive for smokers to select electronic cigarettes in place of real ones.

SUMMARY OF THE INVENTION

In order to overcome various shortcomings in the prior art, some embodiments of the invention provide an improved atomizing electronic cigarette having a liquid permeating component in an atomizer that is sleeved on an electric heater. Cigarette liquid stored in a liquid storage component permeates into the liquid permeating component. The electric heater interacts with the liquid permeating component, such that the cigarette liquid is atomized with smaller and more uniform droplets. In another aspect, by communicating through holes and channels provided and arranged in the electric heater and the liquid storage component, the atomized large drops can adhere to the liquid storage component under the pressure of airflow, such that the inhaled smoke is more similar to the feel a real cigarettes to more suitable meet the taste of smoker.

An embodiment of the invention is an improved atomizing electronic cigarette comprising a power supply unit, a sensor, an atomizing core component and a liquid storage component, within a housing. An air inlet is arranged on the housing. One end of the housing is provided with an air suction port. The atomizing core component comprises an electric heater that can atomize liquid from the liquid storage component.

The liquid storage component can be internally provided with a hollow channel, a through-hole channel, an annular channel or a cross section of sparse mesh channels or combinations thereof, through which gas flows.

The atomizing core component can further comprise a liquid conduction or transportation component in contact with the liquid permeating component and the liquid storage component.

The liquid conduction or transportation component can be sleeved on the liquid permeating component, and include a conduction part that extends from one end of the liquid conduction component in the radial direction to contact with the liquid storage component.

The sensor can be an air pressure sensor or air flow sensor. The housing can comprise a first housing and a second housing, the power device and the sensor are located in the first housing, the atomizing core component and the liquid storage component are located in the second housing, and the auxiliary air inlet is arranged in an area of the first housing and/or the second housing.

The electric heater can be formed by spirally winding electric heating wires or made up of electric heating film arranged on the inner surface of the liquid permeating component, and the electric heater formed by spirally winding or electric heating film on the inner surface of the liquid permeating component can be hollow to form the through hole.

Atomized large drops can be absorbed at, or adhere to, the liquid storage component under the pressure of airflow, a common problem in the prior art where vapor having large particles is passed directly to the user. Thus current embodiments produce inhaled smoke that more closely meets the taste of smoker.

The cigarette liquid can permeate and conduct more sufficiently and rapidly, to more efficiently produce vapor or atomized smoke. In addition, the structure is simple and saves space, such that the volume of the whole atomizing electronic cigarette can be smaller.

In another embodiment of the invention, the electronic cigarette is designed to be detachable and changeable, such that change of components can be simply achieved by detaching and reassembling the first and second housings. Such an electronic cigarette is more convenient to carry as it is also more portable.

DETAILED DESCRIPTION OF THE INVENTION

Figure 1:
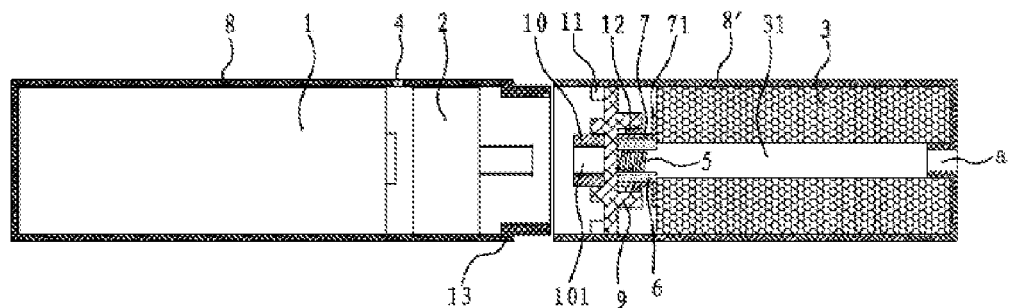
FIG. 1 is a side sectional view of an electronic cigarette according to the invention, showing the first housing separate from the second housing.

The invention will be described in detail below in conjunction with the drawings.

As shown in FIG. 1 to FIG. 5, the invention provides an improved atomizing electronic cigarette, comprising a power device 1, a sensor 2, an atomizing core component and a liquid storage component 3, further comprising a housing containing the above components. An air inlet 4 is arranged on an area of the housing close to the sensor 2. The atomizing core component comprises an electric heater 5 and a liquid permeating component 6 sleeved on the electric heater 5. The electric heater 5 is a hollow structure and has a through hole 51 through which gas flows. The liquid storage component 3 internally has a channel 31 through which the gas flows. The channel can be a hollow channel, a through-hole channel, an annular channel or a channel with mesh cross section or combinations thereof. The purpose is to make the atomized gas that passes through the channel contact with the liquid storage core of the liquid storage component, and to make the liquid storage component 3 coordinate with the liquid permeating component 6 to permeate cigarette liquid to the liquid permeating component 6. In addition, the sensor 2 communicates with the through hole 51 and the channel 31 and forms an airflow loop with the auxiliary air inlet 4.

Figure 2:
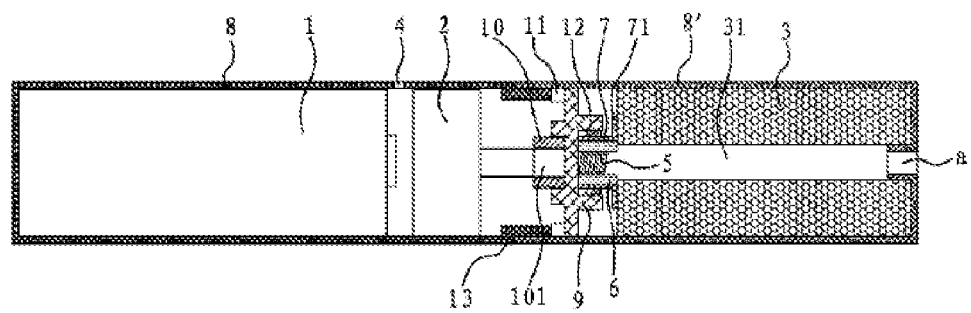
FIG. 2 is a side sectional view of an electronic cigarette according to the invention, showing the first housing connected to the second housing.
Figure 3:
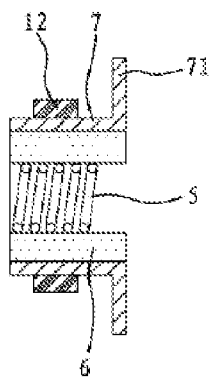
FIG. 3 is a side sectional view of an atomizing core component in an electronic cigarette according to the invention.
Figure 4:
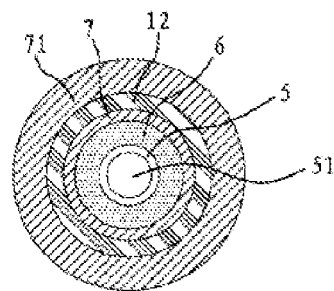
FIG. 4 is a top view of an atomizing core component in an electronic cigarette according to the invention.
Figure 5:
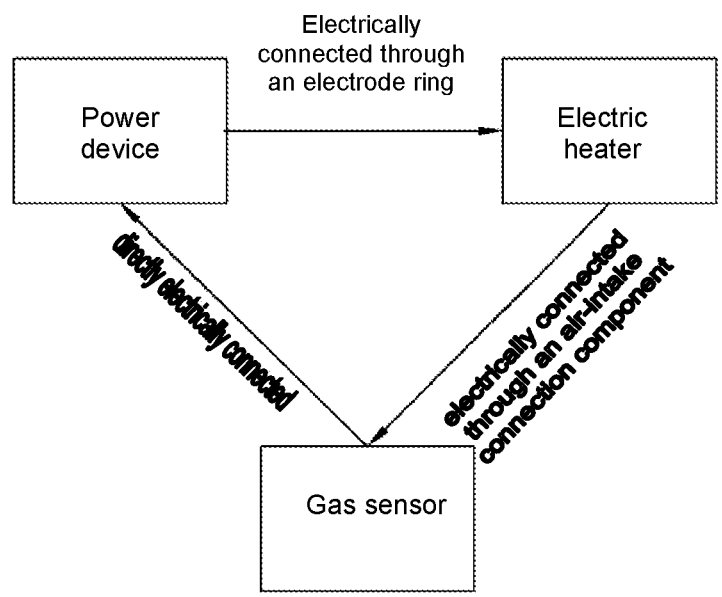
FIG. 5 is an electrical connection block diagram for forming a closed loop among components of an electronic cigarette according to the invention.

In the embodiment, as shown in FIG. 1 to FIG. 3, the atomizing core component further comprises a liquid conduction component 7 that is contacted with the liquid permeating component 6 and with the liquid storage component 3. The liquid conduction component 7 is sleeved on the liquid permeating component 6, with a conduction part 71 that extends from one end of the liquid conduction component in the radial direction, and is contacted with the liquid storage component 3. As a result, cigarette liquid on the liquid storage component 3 is absorbed and permeated to the liquid permeating component. To make the liquid conduction component 7 mate with the liquid permeating component 6 more tightly to improve the liquid conductivity, a fastening sleeve 12 can be sleeved on the liquid conduction component 7.

The sensor 2 can be an air pressure sensor or airflow sensor. In the embodiment, an airflow sensor is used. The housing comprises a first housing 8 and a second housing 8', the power supply unit 1 and the sensor 2 which are located in the first housing 8. The atomizing core component and the liquid storage component 3 are located in the second housing 8'. The auxiliary air inlet 4 is arranged in an area of the first housing 8 and/or the second housing 8' close to the sensor 2. In the embodiment, the auxiliary air inlet 4 is arranged on the first housing 8 and located in an area close to the sensor 2. The power supply unit 1 is a battery that can be a rechargeable battery or disposable battery.

A bracket 9 is arranged in the second housing 8'. The atomizing core component is fixed on the bracket 9, and the electric heater 5 is connected with the power device 1 and the sensor 2 and starts to heat or stops heating according to the flow situation detected by the sensor 2. An air-intake connection component 10 and an electrode ring 11 are arranged on the bracket 9. The air-intake connection component 10 and the electrode ring 11 are electrically connected with two leads of the electric heater 5, respectively. The air-intake connection component 10 achieves an electrical connection through connection with the sensor 2. The electrode ring 11 is electrically connected with the power device 1 through the connection of the air-intake connection component 10 and the sensor 2. The function of the sensor is to switch on or off the whole circuit according to the gas flow. When user inhales, gas inside the electronic cigarette flows. At this time, the sensor switches the circuit on to start the electric heater 5 to heat. When the user stops inhaling, gas stops flowing, and the sensor switches the circuit off to make the electric heater 5 stop heating. An electrode ring post 13 corresponding to the electrode ring 10 is arranged at the opening of the first housing 8. A contact part 131 extends from the electrode ring post 13 in the axial direction. The electrode ring post 13 is connected with the power device 1. When the first housing 8 and the second housing 8' are connected, the contact part 131 is inserted into the second housing 8' and contacted with the electrode ring 11.

In this embodiment, the first housing 8 and the second housing 8' are connected through the connection of the air-intake connection component 10 and the sensor 2, and the air-intake connection component 10 and the sensor 2 are connected by means of splicing or plugging, threads, or clamping. Through such a detachable and changeable split structure, the change of components can be simply achieved by detaching and reassembling the first housing 8 and the second housing 8', such that it is convenient to carry and use the electronic cigarette. This embodiment discloses a connection structure by means of threads.

As shown in FIG. 1, the air-intake connection component 10 also has an air vent 101. The sensor 2 communicates with the air vent 101, the through hole 51 and the channel 31 and forms an airflow path with the auxiliary air inlet 4. An air suction port 32 is arranged on the second housing 8', and the sensor 2 communicates with the air vent 101, the through hole 51, the channel 31 and the air suction port 32 and forms an airflow path with the auxiliary air inlet 4.

The liquid storage component 3 is made of liquid storage core materials such as micro-porous ceramic, foamed ceramic, natural fiber, artificial fiber or foam metal material. The liquid permeating component 6 is made of ceramic fiber, quartz fiber, glass fiber, aramid fiber, common fiber, paper, fabric or non-woven fabric material. The thickness of the liquid permeating component 6 is from 0.5 to 5 mm. The electric heater 5 is formed by spirally winding electric heating wires, which forms the through hole 51. The diameter of the through hole 51 can be from 0.5 to 4 mm. In this embodiment, the thickness of the liquid permeating component 6 is 1 mm, and the diameter of the through hole 51 is 1 mm.

The liquid permeating component 6 in the atomizing core component is directly sleeved on the electric heater 5. Cigarette liquid in the liquid storage component 3 is conducted and permeated to the liquid permeating component 6 by the liquid conduction component 7. The thickness of the liquid permeating component 6 is 1 mm. As a result, the permeated cigarette liquid can be completely vaporized by the electric heater 5 more easily. When the user inhales, as the sensor 2 communicates with the air vent 101, the through hole 51, the channel 31 and the air suction port 32 and forms an airflow path with the auxiliary air inlet 4. When gas flow is generated inside the electronic cigarette, the sensor 3 switches the circuit on, the electric heater 5 starts to heat to make the cigarette liquid in the liquid permeating component 6 be vaporized after reaching the boiling point. At the same time, because the through hole 51 and the channel 31 of the electric heater 5 and the liquid storage component 3 are in communication, vapor generated during atomizing process can be further cooled under the push of airflow and finally inhaled into the user's mouth through the air suction port 32.

Figure 6:
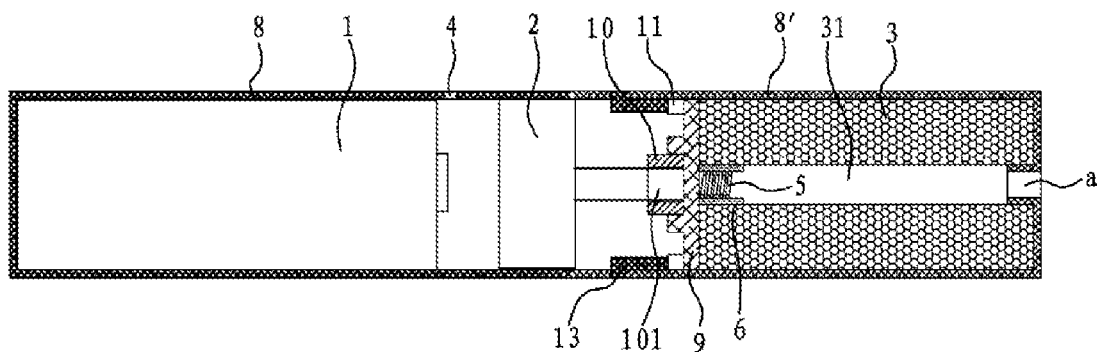
FIG. 6 is a side cutaway view of an electronic cigarette according to another embodiment of the invention.

In another preferred embodiment of the invention, as shown in FIG. 6, the liquid permeating component 6 is contacted with the liquid storage component 3. The atomizing core component is sleeved in the channel 31 of the liquid storage component 3, and the peripheral surface of the liquid permeating component 6 is mated with the inner wall of the channel 31.

The liquid storage component 3 can be made of micro-porous ceramic, foamed ceramic, natural fiber, artificial fiber or foam metal material. The liquid permeating component 6 can be made of ceramic fiber, quartz fiber, glass fiber, aramid fiber, common fiber, paper, fabric or non-woven fabric material. The thickness of the liquid permeating component 6 ranks from 0.5 to 5 mm. The electric heater 5 is formed by spirally winding electric heating wires to form a through hole 51. The diameter of the through hole 51 can be from 0.5 to 4 mm. In this embodiment, the thickness of the liquid permeating component 6 is 1 mm and the diameter of the through hole 51 is 1 mm.

In this embodiment, the atomizing core component is integrally sleeved in the channel 31 of the liquid storage component 3, such that the surface of the liquid permeating component 6 is directly contacted with the inner wall of the channel 31 of the liquid storage component 3. Because the contact area is larger, the permeation and conduction of cigarette liquid is more sufficient and rapid, and the atomized smoke efficiently generated. At the same time, the structure is simple and saves space, so as to minimize the size of the atomizing electronic cigarette.

In other embodiments, an improved atomizing electronic cigarette is provided comprising a power device (1), a sensor (2), an atomizing core component and a liquid storage component (3), further comprising a housing containing the above components, an auxiliary air inlet (4) being arranged on the housing. One end of the housing is provided with an air suction port, characterized in that the atomizing core component comprises an electric heater (5), the electric heater (5) atomizes liquid in a liquid storage component (3). The liquid storage component (3) internally has a channel (31) through which the atomized gas flows, and the auxiliary air inlet (4), the sensor (2) and the suction nozzle form an airflow loop.

In other aspects the atomizing electronic cigarette can be characterized in that the atomizing core component comprises a liquid permeating component (6) that is sleeved on the electric heater (5), a channel (51) through which gas flows is arranged in the atomizing core component, and the channel (51) is made up of the structure of the electric heater (5).

In other aspects the atomizing electronic cigarette can be characterized in that the electric heater (5) of the atomizing core component is directly inserted into the channel (31) of the liquid storage component (3), and the atomized gas directly flows through the channel (31).

In other aspects the atomizing electronic cigarette is characterized in that the liquid storage component (3) is internally provided with the channel (31) which is a hollow channel, a through-hole channel, an annular channel or a channel with mesh in cross section or combinations thereof, through which gas flows.

In other aspects the atomizing electronic cigarette is characterized in that the atomizing core component further comprises a liquid conduction component (7) that is contacted with the liquid permeating component (6), and with the liquid storage component (3).

In other aspects, the atomizing electronic cigarette is characterized in that the liquid conduction component (7) is sleeved on the liquid permeating component (6), a conduction part (71) extends from one end of the liquid conduction component in the radial direction, and the conduction part (71) is contacted with the liquid storage component (3).

In other aspects, the atomizing electronic cigarette is characterized in that the sensor (2) is an air pressure sensor or airflow sensor, the housing comprises a first housing (8) and a second housing (8'), the power device (1) and the sensor (2) are located in the first housing (8), the atomizing core component and the liquid storage component (3) are located in the second housing (8'), and the auxiliary air inlet (4) is arranged in an area of the first housing (8) and/or the second housing (8') close to the sensor.

In other aspects, the atomizing electronic cigarette is characterized in that a bracket (9) is arranged in the second housing (8'), the atomizing core component is fixed on the bracket (9), and the electric heater (5) is connected with the power device (1) and the sensor (2) and starts to heat or stops heating according to the flow situation of gas through the sensor (2).

In other aspects, the atomizing electronic cigarette is characterized in that an air-intake connection component (10) and an electrode ring (11) are arranged on the bracket (9), the air-intake connection component (10) and the electrode ring (11) are electrically connected with two leads of the electric heater (5) respectively, the air-intake connection component (10) achieves electric connection through connection with the sensor (2), the electrode ring (11) is electrically connected with the power device (1) through the connection of the air-intake connection component (10) and the sensor (2), the air-intake connection component (10) also has an air vent (101), the sensor (2) communicates with the air vent (101), the through hole (51) and the channel (31) and forms an airflow path with the auxiliary air inlet (4).

In other aspects, the atomizing electronic cigarette is characterized in that the first housing (8) and the second housing (8') are connected through the connection of the air-intake connection component (10) and the sensor (2), and the air-intake connection component (10) and the sensor (2) are connected by means of splicing or plugging, threads or clamping.

In other aspects, the atomizing electronic cigarette is characterized in that an air suction port (a) is arranged on the second housing (8'), and the sensor (2) communicates with the air vent (101), the through hole (51), the channel (31) and the air suction port (a) and forms an airflow loop with the auxiliary air inlet (4).

In other aspects, the atomizing electronic cigarette is characterized in that the housing is an integrated whole, the front end of which is provided with the auxiliary air inlet (4), and the sensor (2) communicates with the air vent (101), the through hole (51), the channel (31) and the air suction port (a) and forms an airflow loop with the auxiliary air inlet (4).

In other aspects, the atomizing electronic cigarette is characterized in that the liquid permeating component (6) is contacted with the liquid storage component (3), the atomizing core component is sleeved in the channel (31) of the liquid storage component (3), and the peripheral surface of the liquid permeating component (6) is mated with the inner wall of the channel (31).

In other aspects, the atomizing electronic cigarette is characterized in that the liquid storage component (3) is made of micro-porous ceramic, foamed ceramic, natural fiber, artificial fiber or foam metal material, the liquid permeating component (6) is made of ceramic fiber, quartz fiber, glass fiber, aramid fiber, common fiber, paper, fabric or non-woven fabric material, the electric heater (5) is formed by spirally winding electric heating wires or made up of electric heating film arranged on the inner surface of the liquid permeating component, and the electric heater formed by spirally winding or electric heating film on the inner surface of the liquid permeating component is hollow to form the through hole (51).

In other aspects, the atomizing electronic cigarette is characterized in that the thickness of the liquid permeating component (6) ranks from 0.5 to 5 mm, and the diameter of the through hole (51) ranks from 0.5 to 4 mm.

In other aspects, the atomizing electronic cigarette is characterized in that zeolite particles are added in the liquid permeating component (6).

I claim:

1. An electronic cigarette, comprising:
a first housing having a battery;
a second housing attached to the first housing, the second housing including an inhalation port;
a liquid storage component and an atomizing core in the second housing, the atomizing core including a wire coil electrically connectable to the battery for atomizing liquid from the liquid storage component;
the atomizing core centrally supported in the second housing on a bracket; and
a channel extending through and surrounded by the liquid storage component, with the channel and the inhalation port forming an airflow path centrally located within the second housing, and with the channel providing a continuous passageway from the wire coil to the inhalation port.

2. The electronic cigarette of claim 1 further including an air-intake connection component and an electrode ring on the bracket, the wire coil electrically connected to the battery through the electrode ring.

3. The electronic cigarette of claim 2 further including a ring post in the first housing engageable with the electrode ring.

4. The electronic cigarette of claim 3 further including a contact part on the electrode ring post extending axially and contacting the electrode ring.

5. The electronic cigarette of claim 1 further a sensor in the first housing electrically connected to the battery.

6. The electronic cigarette of claim 5 further comprising an auxiliary air inlet in the first housing leading into the channel via an air vent through the bracket.

7. The electronic cigarette of claim 1 wherein the wire coil is in the channel.

8. The electronic cigarette of claim 7 wherein the wire coil is surrounded by the liquid storage component.

9. The electronic cigarette of claim 7 wherein the wire coil is at a first end of the channel.

10. The electronic cigarette of claim 1 further comprising a liquid conduction component having an axial section and a radial section, the radial section contacting an end of the liquid conduction component.

11. The electronic cigarette of claim 10 further comprising a liquid permeating component sleeved on wire coil and in contact with the axial section of the liquid conduction component.

12. An electronic cigarette, comprising:
a first housing having a battery;
a sensor in the first housing electrically connected to the battery;
a second housing attached to the first housing, the second housing including an inhalation port;
a liquid storage component and an atomizing core in the second housing, the atomizing core including a wire coil electrically connectable to the battery for atomizing liquid from the liquid storage component;
the atomizing core centrally supported in the second housing on a bracket;
an electrode ring on the bracket;
a ring post in the first housing engageable with the electrode ring, the wire coil electrically connected to the battery through the ring post and the electrode ring; and
a channel extending through and surrounded by the liquid storage component, with the channel and the inhalation port forming an airflow path centrally located within the second housing, and with the channel providing a continuous unobstructed passageway from the wire coil to the inhalation port.

* * * * *